(12) United States Patent
Quy

(10) Patent No.: US 8,700,009 B2
(45) Date of Patent: Apr. 15, 2014

(54) METHOD AND APPARATUS FOR MONITORING EMOTION IN AN INTERACTIVE NETWORK

(75) Inventor: Roger J. Quy, Kentfield, CA (US)

(73) Assignee: Q-Tec Systems LLC, Wilmington, DE (US)

( * ) Notice: Subject to any disclaimer, the term of this patent is extended or adjusted under 35 U.S.C. 154(b) by 151 days.

(21) Appl. No.: 13/151,711

(22) Filed: Jun. 2, 2011

(65) Prior Publication Data

US 2011/0300847 A1    Dec. 8, 2011

Related U.S. Application Data

(60) Provisional application No. 61/350,651, filed on Jun. 2, 2010.

(51) Int. Cl.
*H04M 3/42* (2006.01)
*A61B 5/00* (2006.01)

(52) U.S. Cl.
USPC .......................... 455/414.1; 600/300; 600/301

(58) Field of Classification Search
USPC ................................ 455/414.1; 600/300, 301
See application file for complete search history.

(56) References Cited

U.S. PATENT DOCUMENTS

| | | | |
|---|---|---|---|
| 6,190,314 B1 | 2/2001 | Ark et al. | |
| 6,358,201 B1 | 3/2002 | Childre et al. | |
| 6,648,822 B2 | 11/2003 | Hamamoto et al. | |
| 6,656,116 B2 | 12/2003 | Kim et al. | |
| 7,331,870 B2 | 2/2008 | Smith et al. | |
| 7,462,151 B2 | 12/2008 | Childre et al. | |
| 7,547,279 B2 * | 6/2009 | Kim et al. | 600/300 |
| 7,785,197 B2 | 8/2010 | Smith | |
| 7,822,816 B2 | 10/2010 | Payne | |
| 7,874,983 B2 | 1/2011 | Zancho et al. | |

(Continued)

FOREIGN PATENT DOCUMENTS

| | | | | |
|---|---|---|---|---|
| KR | 1020030034424 A | | 9/2003 | |
| KR | 1020050002161 | * | 7/2006 | ............... H04Q 7/24 |

(Continued)

OTHER PUBLICATIONS

Jennifer Healey, "Physiological User Interfaces", IBM T.J. Research Center, pp. 1-5.

(Continued)

*Primary Examiner* — Wesley Kim
(74) *Attorney, Agent, or Firm* — Mayer & Williams PC; Mark D. Wieczorek

(57) ABSTRACT

Embodiments of the invention provide a method, devices, and system for monitoring and sharing emotion-related data from one or more persons connected via the internet. An emotion monitoring device (EMD) measures physiological signals obtained from biosensors and computes emotion states relating to emotional arousal and valence. Various signal processing methods are employed to reduce artifact and improve the detection of emotional states. The EMD communicates the emotion data to an internet server via a wireless network. The internet server transmits the emotion data to other persons equipped with an EMD. Their emotion data similarly is obtained and shared with others. The networked emotion data can used to enrich online, community experiences such as games and social networks. An implementation of an EMD based on a smart phone enables emotion data to be monitored in wide area, mobile environment. The biosensors can be integrated into the casing or a cover for the mobile phone.

16 Claims, 5 Drawing Sheets

(56) References Cited

U.S. PATENT DOCUMENTS

| | | |
|---|---|---|
| 2003/0149344 A1 | 8/2003 | Nizan |
| 2004/0117212 A1 | 6/2004 | Kong et al. |
| 2005/0004923 A1* | 1/2005 | Park ................... 707/100 |
| 2005/0240956 A1 | 10/2005 | Smith et al. |
| 2007/0270663 A1 | 11/2007 | Ng et al. |
| 2008/0091512 A1 | 4/2008 | Marci et al. |
| 2008/0214903 A1 | 9/2008 | Orbach |
| 2008/0221401 A1 | 9/2008 | Derchak et al. |
| 2009/0088610 A1 | 4/2009 | Lee et al. |
| 2009/0128487 A1* | 5/2009 | Langereis et al. ............ 345/157 |
| 2009/0177607 A1* | 7/2009 | Matsushima ................... 706/46 |
| 2009/0281400 A1 | 11/2009 | McCraty et al. |
| 2010/0004977 A1 | 1/2010 | Marci et al. |
| 2010/0113152 A1 | 5/2010 | Shmuel |
| 2010/0113950 A1 | 5/2010 | Lin et al. |
| 2010/0160797 A1* | 6/2010 | Banet et al. ................... 600/485 |
| 2010/0268056 A1* | 10/2010 | Picard et al. ................... 600/388 |
| 2011/0040155 A1 | 2/2011 | Guzak et al. |
| 2011/0105857 A1 | 5/2011 | Zhang et al. |
| 2011/0301435 A1* | 12/2011 | Albert et al. ................... 600/301 |

FOREIGN PATENT DOCUMENTS

| | | |
|---|---|---|
| KR | 1020060081759 A | 7/2006 |
| KR | 1020070087787 A | 2/2007 |
| KR | 1020100128023 A | 7/2010 |
| WO | 9733515 A1 | 9/1997 |
| WO | 2006090371 A2 | 8/2006 |
| WO | 2008028391 A1 | 3/2008 |
| WO | 2008055078 A2 | 5/2008 |
| WO | 2010104480 A1 | 9/2010 |

OTHER PUBLICATIONS

Jianhua Tao et al., "Affective Information Processing", (c) Springer-Verlag London Limited 2009, pp. V-VIII and 1-8.

Christian Peter et al., "Physiological Sensing for Affective Computing", (c) Springer Science+Business Media LLC 2008, pp. 293-310.

International Search Report from corresponding PCT Application No. PCT/US2011/038883, dated Feb. 23, 2012, 13 pages.

\* cited by examiner

METHOD AND APPARATUS FOR MONITORING EMOTION IN AN INTERACTIVE NETWORK

CROSS-REFERENCE TO RELATED APPLICATIONS

This application claims benefit of priority to U.S. Provisional Application Ser. No. 61/350,651, filed Jun. 2, 2010, which is incorporated herein by reference in its entirety.

FIELD OF THE INVENTION

The present invention relates to monitoring the emotions of persons using biosensors and sharing such information with others over the internet.

BACKGROUND OF THE INVENTION

It is known that human emotional states have underlying physiological correlates reflecting activity of the autonomic nervous system. A variety of physiological signals have been used to detect emotional states. However, it is not easy to use physiological data to monitor emotions accurately because physiological signals are susceptible to artifact, particularly with mobile users, and the relationship between physiological measures and positive or negative emotional states is not straightforward.

A standard model separates emotional states into two axes: arousal (e.g. calm-excited) and valence (negative-positive]. Thus emotions can be broadly categorized into high arousal states, such as fear/anger/frustration (negative valence) and joy/excitement/elation (positive valence); or low arousal states, such as depressed/sad/bored (negative valence) and relaxed/peaceful/blissful (positive valence).

SUMMARY OF THE INVENTION

Implementations of this invention overcome certain of the disadvantages of the prior art by incorporating a number of features to reduce artifact and improve the detection and monitoring of emotional states. In implementations of this invention, emotion recognition algorithms, based on reports from several years of research and testing with military and clinical subjects, derive emotion arousal and valence indices from physiological signals. Emotion-related data are calculated from physiological signals and communicated to and from a software application running on a server connected to the internet. In one implementation, emotion data from multiple persons may be shared in an interactive network.

Previous systems to detect emotions have typically been designed for laboratory use and are based on a computer. In contrast, this system is designed for personal use and can be based on a smart mobile device, e.g. iPhone®, thus enabling emotions to be monitored in everyday surroundings. Moreover, the system is designed for multiple users that can be connected in an interactive network whereby emotion data can be collected and shared. The sharing of emotion data, made possible by cellular communications, can be a way to enrich the experiences of users interacting with a variety of social communities, media and, entertainment.

People are often not aware of transient emotional changes so monitoring emotional states can enrich experiences for individuals or groups. One application of this system is for entertainment, such as using emotion data for interactive gaming, or interactive television and movies. Another application is for personal training—for example, learning to control emotions and maintain a healthy mental attitude for stress management, yoga, meditation, sports peak performance and lifestyle or clinical management. Others have used physiological signals such as heart rate and skin conductance (also known as galvanic skin response or GSR), for biofeedback training or to control games and other software. In implementations of this invention, the physiological data are processed to obtain metrics for emotional arousal level and/or valence that provide the control signals for feedback and interactivity.

Multiple users equipped with emotion monitors can be connected directly, in peer-to-peer networks or via the internet, with shared emotion data. Applications include multi-player games, on-line dating services, team sports, or other group activities. With many users connected in a network, emotion data can enhance social games, media, and communities. The emotion data can be captured and analyzed for marketing purposes. Emotion ratings can be collected via the internet for a variety of media, including written content, graphics, photographs, video and music. Emotional reactions to other sensory input such as taste and olfactory tests could also be obtained.

In more detail, implementations of the invention provide systems and methods for interactive monitoring of emotion by recording one or more physiological signals, in some cases using simultaneous measurements, and processing these signals with a novel emotion detection algorithm, providing a display of emotion data, and using the data to interact with games and other software. The emotion data can be transmitted to an internet server and shared by more than one user to form an emotion network for interactive games and social communities.

Biosensors record physiological signals that relate to changes in emotional states, such as skin conductance, skin temperature, respiration, heart rate, blood volume pulse, blood oxygenation, electrocardiogram, electromyogram, and electroencephalogram. For a variety of these signals, either wet or dry electrodes are utilized. Alternatively, photoplethysmography (PPG), which utilizes a light source and light sensor, can be employed, e.g., to record heart pulse rate and blood volume pulse. The biosensors can be deployed in a variety of forms, including a finger pad, finger cuff, ring, glove, ear clip, wrist-band, chest-band, or head-band. The sensors can be integrated into the casing of a mobile game console or controller, a TV remote, a computer mouse, or other hand-held device; or into a cover that fits onto a hand-held device, e.g., a mobile phone. In some cases, the biosensors may be integrated into an ancillary game controller that is in turn in signal communication with a standard game controller. For example, the biosensors may be integrated into a Wii® Nunchuk, and the same is then plugged into a Wii® Remote™ or Balance Board™ In some implementations, the biosensors may be particularly useful in motion controllers such as the Xbox® Kinect™, or Sony® Move™.

In some implementations of the invention, a plurality of biosensors may simultaneously record physiological signals, and the emotion algorithm may receive these plurality of signals and employ the same in displaying emotion data in responding to the emotion data, such as for an emotion network or for the control of interactive games. In such cases, a plurality of biosensors may be employed to detect and employ emotion signals in the game, or some biosensors may be used for the motion signal analysis while others are used for other analysis, such as motion or the like.

Physiological signals are easily contaminated by noise from a variety of sources, especially movement artifacts. A variety of methods are used to improve the signal to noise ratio and remove artifact. Electrical biosensors include electromagnetic shielding, e.g., a Faraday cage, to reduce environmental noise. Since the contact between the biosensor and underlying skin could be poor (e.g. through clothing or hair), the signals are coupled to a very high-impedance input amplifier. Capacitive-coupled biosensors can be used in some applications. Another strategy is to use an array of biosensors in the place of one, which allows for different contact points or those with the strongest signal source to be selected, and others used for artifact detection and active noise cancellation. An accelerometer can be attached to the biosensor to aid monitoring and cancellation of movement artifacts.

The signal is further processed to enhance signal detection and remove artifacts using algorithms based on blind signal separation methods and state of the art machine learning techniques. By way of illustration, when detecting beat-to-beat heart rate from a biosensor designed for everyday use by consumers (in contrast to the medical sensors typically used in a clinical or research setting) the heart QRS complexes are identified via a hybrid pattern recognition and filter-bank method with dynamic thresholding. Heart beats thus detected are then fed to a probabilistic (Bayesian) tracking algorithm based on Gauss-Hermite, Kalman filtering, thereby increasing robustness to noise and insensitivity to ECG arrhythmia while maintaining responsiveness to rapidly changing heart rates. Such signal processing may be particularly useful in cleaning data measured by such biosensors, as user movement can be a significant source of noise and artifacts.

The physiological signals are transmitted to an emotion monitoring device (EMD) either by a direct, wired connection or wireless connection. Short range wireless transmission schemes may be employed, such as a variety of 802.11 protocols (e.g. Wi-Fi), 802.15 protocols (e.g. Bluetooth® and Zigbee™), other RF protocols, (e.g. ANT), telecommunication schemes (e.g. 3G, 4G) or optical (e.g., infra-red) methods. The EMD can be implemented on a number of devices, such as a mobile phone, game console, netbook computer, tablet computer, laptop, personal computer, or proprietary hardware. The EMD processes the physiological signals to derive and display emotion data, such as arousal and valence components. Others have used a variety of apparatus and methods to monitor emotion, typically some measure reflecting activation of the sympathetic nervous system, such as indicated by changes in skin temperature, skin conductance, respiration, heart rate variability, blood volume pulse, or EEG. Deriving emotion valence (e.g., distinguishing between different states of positive and negative emotional arousal) is more complex.

Implementations of the invention may employ algorithms to provide a map of both emotional arousal and valence states from physiological data. In one example of an algorithm for deriving emotional states the arousal and valence components of emotion are calculated from measured changes in skin conductance level (SCL) and changes in heart rate (HR), in particular the beat-to-beat heart rate variability (HRV). Traditionally, valence was thought to be associated with HRV, in particular the ratio of low frequency to high frequency (LF/HF) heart rate activity. By combining the standard LF/HF analysis with an analysis of the absolute range of the HR (max-min over the last few seconds), emotional states can be more accurately detected. By way of illustration, one algorithm is as follows: If LF/HF is low (calibrated for that user) and/or the heart rate range is low (calibrated for that user) this indicates a negative emotional state. If either measurement is high, while the other measurement is in a medium or a high range, this indicates a positive state. A special case is when arousal is low; in this case LF/HF can be low, while if the HR range is high, this still indicates a positive emotional state. The accuracy of the valence algorithm is dependent on detecting and removing artifact to produce a consistent and clean HR signal.

A method of SCL analysis is also employed for deriving emotional arousal. A drop in SCL generally corresponds to a decrease in arousal, but a sharp drop following a spike indicates high, not low, arousal. A momentary SCL spike can indicate a moderately high arousal, but a true high arousal state is a series of spikes, followed by drops. Traditionally this might be seen as an increase, then decrease in arousal, but should instead be seen as a constantly high arousal. Indicated arousal level should increase during a series of spikes and drops, such that the most aroused state, such as by Anger if in negative valence, requires a sustained increase, or repeated series of increases and decreases in a short period of time, not just a single large increase, no matter the magnitude of the increase. The algorithm can be adapted to utilize BVP as the physiological signal of arousal.

The above-described emotion-deriving algorithms are believed to have certain advantages in certain implementations of the invention. However, other ways of deriving emotion variables may also be employed. As may be seen above, these algorithms generally derive emotion data, which may include deriving values for individual variables such as level of stress. However, they also can generally derive a number of other emotion variables, and as such may be thought of as occupying an abstraction layer above, e.g., devices that propose to calculate a single variable such as stress from measurements of skin conductance or heart rate variability. The emotion-deriving algorithms may be implemented in a software application running in the EMD, or in firmware, e.g. a programmable logic array, read-only memory chips, or other known methods.

The system is designed to calibrate automatically each time it is used; also baseline data are stored for each user so the algorithm improves automatically as it learns more about each user's physiological profile. Accuracy of emotion detection is improved with the addition of more physiological data—such as skin temperature, respiration, or EEG.

The emotional arousal and valence data can be expressed in the form of a matrix displaying emotional states. The quadrants in the matrix can be labeled to identify different emotional states depending on the algorithm, e.g., feeling "angry/anxious, happy/excited, sad/bored, relaxed/peaceful". The data can be further processed to rotate the axes, or to select data subsets, vectors, and other indices such as "approve/disprove", "like/dislike", "agree/disagree", "feel good/feel bad", "good mood/bad mood", "calm/stressed"; or to identify specific emotional states, such as being "centered" or "in the zone" (e.g., for sports peak performance). The emotional states and scores can be validated against standard emotional stimuli (e.g., the International Affective Picture System). In addition with large data sets, techniques such machine learning, data mining, or statistical analysis can be used to refine the analysis and obtain specific emotional response rating scales.

It can be helpful for emotion data to be displayed to the user in graphical form. Other visual or auditory feedback can be utilized, such as a color code or symbol (e.g. "emoticon") representing the emotional states. The emotion data optionally may then be transmitted to an internet server, or cloud infrastructure, via a wired or wireless telecommunication network. An internet server can send a response back to the user; and with multiple users, the emotion data of one user can be transmitted from the server to be displayed on the EMD of other users. The server application program stores the emotion data and interacts with the users, sharing emotion data among multiple users as required. The emotion data may be incorporated in local, multiplayer, and social games or online communities that have been designed or adapted to interact with a user's emotional response, so that characters, events, objects or other players can respond to a player's emotions. Additionally, emotion data can be obtained, transmitted, analyzed, and displayed in response to online content that is downloaded to the EMD. The emotion rating scores can be statistically manipulated, analyzed, or made available to social communities and on-line search engines, as required.

DETAILED DESCRIPTION OF THE PREFERRED EMBODIMENTS

Various acronyms are used for clarity herein. Definitions are given below.

The term "subject" as used herein indicates a human subject. The term "user" is generally used to refer to the user of the device, which may be synonymous with the subject. The term "signal communication" is used to mean any type of connection between components that allows information to be passed from one component to another. This term may be used in a similar fashion as "coupled", "connected", "information communication", "data communication", etc. The following are examples of signal communication schemes. As for wired techniques, a standard bus, serial or parallel cable may be used if the input/output ports are compatible and an optional adaptor may be employed if they are not. As for wireless techniques, radio frequency (RF) or microwaves, and optical techniques, including lasers or infrared (IR, and other such techniques may be used. A variety of methods and protocols may be employed for short-range, wireless communication including IEEE 802 family protocols, such as Bluetooth® (also known as 802.15), Wifi (802.11), ZigBee™, Wireless USB and other personal area network (PAN) methods, including those being developed. For wide-area wireless telecommunication, a variety of cellular, radio satellite, optical, or microwave methods may be employed, and a variety of protocols, including IEEE 802 family protocols (e.g. 802.11, 802.16, or 802.20), Wi-Fi, WiMax, UWB, Voice over IP (VOIP), Long-Term Evolution (LTE), and other wide-area network or broadband transmission methods and communication standards being developed. It is understood that the above list is not exhaustive.

Various embodiments of the invention are now described in more detail.

Figure 1:
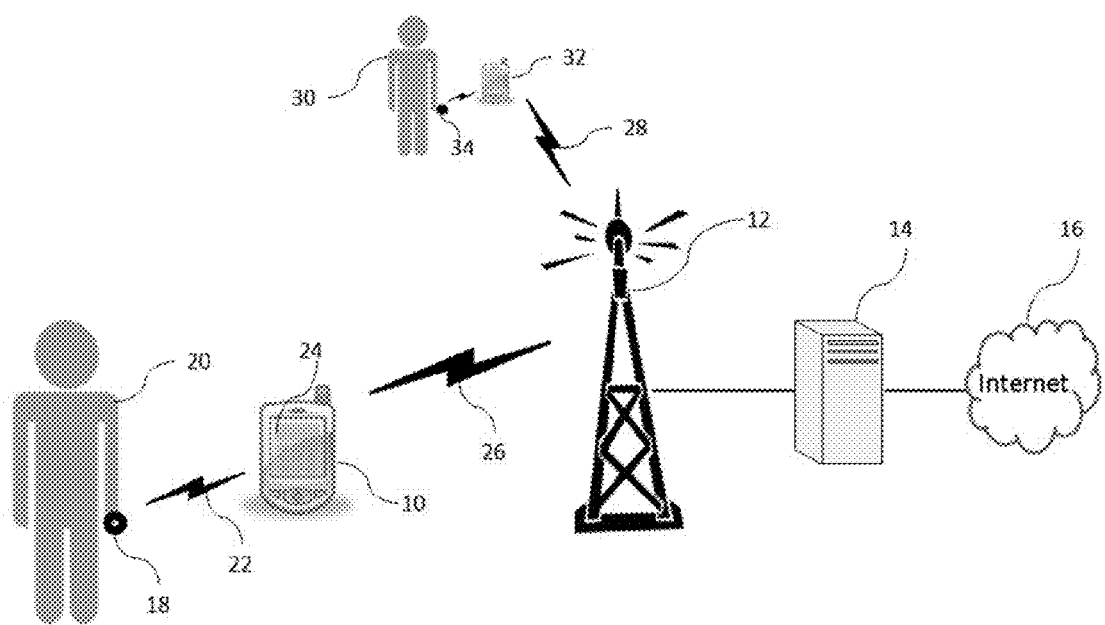
FIG. 1 illustrates a general embodiment of an emotion monitoring network according to the present invention.

Referring to FIG. 1, a system of the present invention is shown for monitoring emotion data from one or more subjects connected in a network. A subject 20 is in contact with one or more biosensors 18 to record physiological signals. The biosensors can be deployed in a variety of forms, including a finger pad, finger cuff, ring, glove, ear clip, wrist-band, chestband, or head-band. Other varieties of biosensors will also be understood. The physiological signals are transmitted to an emotion monitoring device (EMD) 10 by a wired or short-range wireless connection 22. As described above, EMD 10 further processes the physiological signals and an algorithm derives emotion data from the signals, such as arousal and valence indices. Screen 24 displays emotion data to subject 18.

EMD 10 is connected to a telecommunication network 12 via a wide area, wired or wireless connection 26. The telecommunication network 12 is connected to a server 14 that is part of the internet infrastructure 16. EMD 10 optionally transmits the emotion data to a website associated with an application program running on computer readable media (CRM) in server 14, which receives, processes and responds to the data. The computer readable media in server 14 and elsewhere may be in non-transitory form. A response can be transmitted back to EMD 10. The server may also transmit emotion data via connection 28 to be displayed to other remote subjects 30. The remote subjects 30 are equipped with an EMD 32 and biosensors 34 and may similarly transmit their emotion data to an internet server 14. The server application program stores the emotion data and interacts with the users, including sharing emotion data among the network of users as required for activities such as games and enriching social networks [see FIG. 5].

Figure 2:
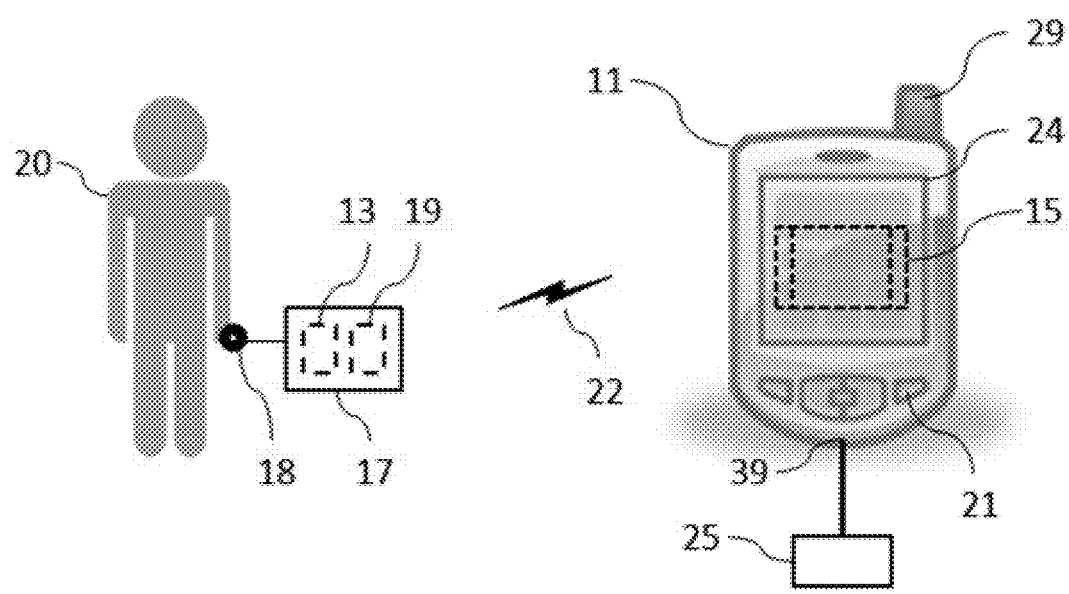
FIG. 2 illustrates an embodiment of an emotion monitoring device based on a mobile phone wirelessly connected to biosensors.

Referring to FIG. 2, an embodiment of EMD 10 is shown based on a web-enabled, mobile phone 11. One or more biosensors 18 measure physiological signals from a subject 20. A variety of types of biosensors may be employed that measure signals related to changes in emotional states, such as skin conductance, skin temperature, heart rate, blood volume pulse, blood oxygenation, ECG, and EEG. For a variety of these signals, either wet or dry electrodes, or alternatively, PPG optical sensors can be employed. Implantable sensors may also be employed. The biosensors are incorporated in a finger pad, finger ring, ear clip (e.g. attached to a phone earpiece), wrist-band, chest-band, head-band, or adhesive patch as a means of attaching the biosensors to the subject. The signals are amplified and processed to reduce artifact in a signal processing unit (SPU) 17. An accelerometer 13 optionally may be included to aid monitoring and cancellation of movement artifacts. A short-range wireless transmitter 19 is employed to transmit the signals via connection 22 (e.g., Bluetooth®) to a web-enabled, mobile phone 11 (e.g. iPhone®). An optional adapter 25 connected to the generic input/output port or "dock connector" 39 of the mobile phone may be employed to receive the signals. Alternatively, SPU 17 can connect by means of a direct or wired connection to the mobile phone. An application program 15 is downloaded from an internet server to a CRM in the mobile phone. The application program receives and processes the physiological signals and includes an algorithm to derive emotion data. The program includes a user interface to display the emotion data on screen 24, and for the subject to manually enter information by means of a keyboard, buttons or touch screen 21. As illustrated in FIG. 1, the mobile phone 11 optionally transmits the emotion data via antenna 29 to the internet server, and may receive emotion data of other users.

It will be clear to one of ordinary skill in the art given this teaching that mobile phone 11 may be replaced with other types of wireless devices such as a tablet computer, laptop computer, PC, game controller, TV remote controller, computer mouse, or other hand-held device, such as proprietary hardware, provided that such devices have equivalent functionality. The advantage of a web-enabled wireless phone (in contrast to a personal computer or video game console) is that it enables a user's emotions to be monitored and shared with others when the user is fully mobile in a wide-area environment, such as walking around a store. However, the limited amount of memory, processing capability, and display size available on a mobile phone in comparison to a computer (PC) constrains the functionality of the software running on the phone. Application program 15 is thus designed to suit the functional constraints of mobile phone 11. In the case of an emotion network that might encompass a large number of users, it is important that the internet infrastructure is employed for significant application processing and storage of emotion data so that less memory and processing capabilities become necessary on the mobile phone, thus freeing memory and processing for receiving physiological signals and calculating the related emotion data.

The advent of web-enabled mobile phones has brought increased functionality for sending and receiving data from the internet. A web-enabled or smart phone (e.g. iPhone®) is distinguished from conventional cellular phones by features such as a web browser to access and display information from internet web sites. In addition, modern, web-enabled mobile phones run complete operating system software that provides a platform for, mobile application programs or "apps". Third party applications, such as described here, can be downloaded immediately to the phone from a digital distribution system website (e.g. iTunes®) over a wireless network without using a PC to load the program. With increased functionality, the smart phone operating systems can run and multitask applications that are native to the underlying hardware, such as receiving data from an input port and from the internet, at the same time as running other applications using the data. Similarly, a web-enabled tablet (e.g., iPad®) has the advantage of enhanced mobility, by reason of compactness, in contrast to a conventional desktop or even laptop computer; and it has the advantages of an operating system that can run a web browser, download apps from a web site, and multitask application programs, e.g. simultaneously receiving data and running a program to access an online social network, in contrast to a conventional personal digital assistant (PDA).

Figure 3:
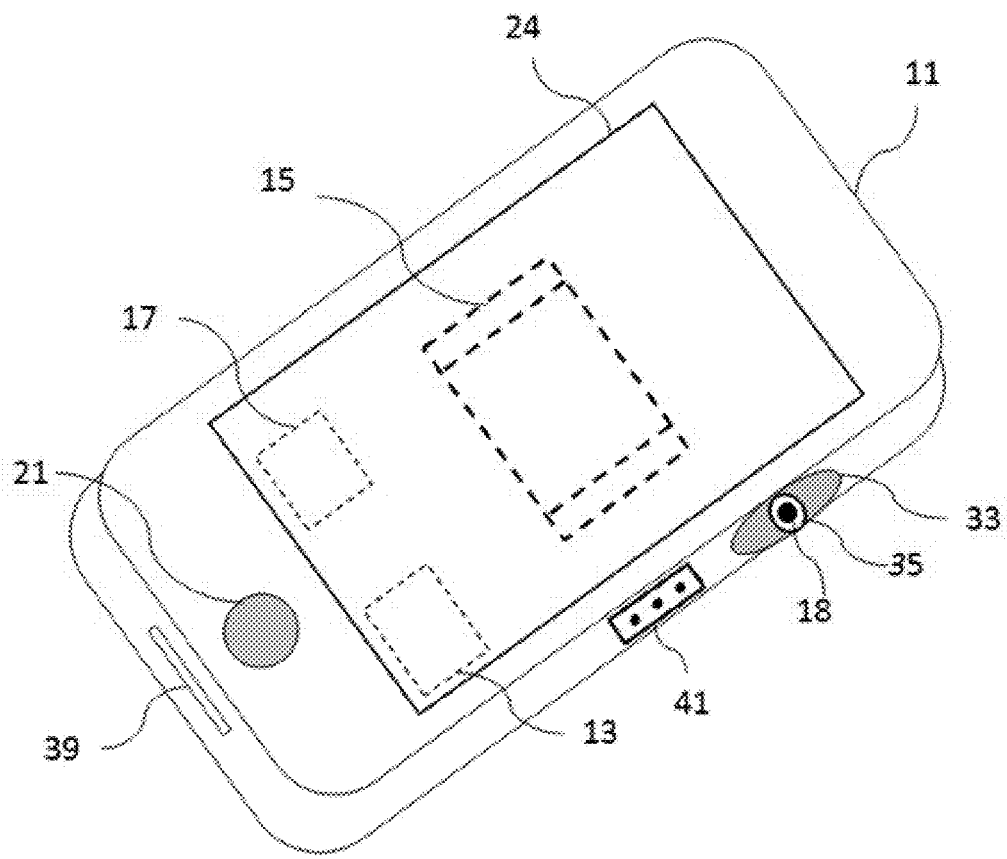
FIG. 3 illustrates an embodiment of an emotion monitoring device based on biosensors integrated into the casing of a mobile phone.

Referring to FIG. 3, an embodiment of EMD 10 is shown based on a web-enabled, mobile phone 11 with biosensors integrated into the casing of the phone. The phone incorporates one or more biosensors 18 to measure physiological parameters that relate to changes in emotional states, such as skin conductance, skin temperature, heart rate, blood volume pulse, blood oxygenation, and electrocardiogram. For a variety of these signals, either wet or dry electrodes, or optical sensors, are utilized. The biosensors may be located in a depression 33 to facilitate finger contact. Alternatively, there may be an array of biosensors, conductive strip, optical fibers, or other means 41 to enable a subject's fingers to be in different positions but still connect to the biosensors, and which allows those biosensors with the strongest signal source to be selected and others used for artifact detection or noise cancellation. A pressure or touch-sensitive sensor 35 in juxtaposition to the biosensors measures finger contact to assist in the detection of artifact. The biosensors are connected to a SPU 17 which amplifies and processes the physiological signals to remove artifact using techniques described above. An accelerometer 13 may be included to aid monitoring and cancellation of movement artifacts.

An application program 15 is downloaded to mobile phone 11 to derive and display emotion data on screen 24 as previously described. The emotion-deriving algorithms may be implemented in firmware in the mobile phone, in which case the application program receives and displays the emotion data. The emotion data may be integrated with other features of the application, such as a game or personal training program. The emotion data optionally may be transmitted to an internet server, and the emotion data of other users displayed as in the first embodiment. It will be clear to one of ordinary skill in the art given this teaching that biosensors may similarly be integrated into other types of handheld devices in place of mobile phone 11, such as a tablet, laptop computer, PC, game controller, TV remote controller, computer mouse, or toy, provided that such devices have equivalent functionality. In some cases, the biosensors may be integrated into an ancillary game controller, that is in turn in signal communication with a standard game controller or console, which runs an application program to receive and display the emotion data. As in the case with an application on the mobile phone, the standard game controller or console may download emotion monitoring and emotion community applications from the internet, as well as display applications for such data.

Figure 4:
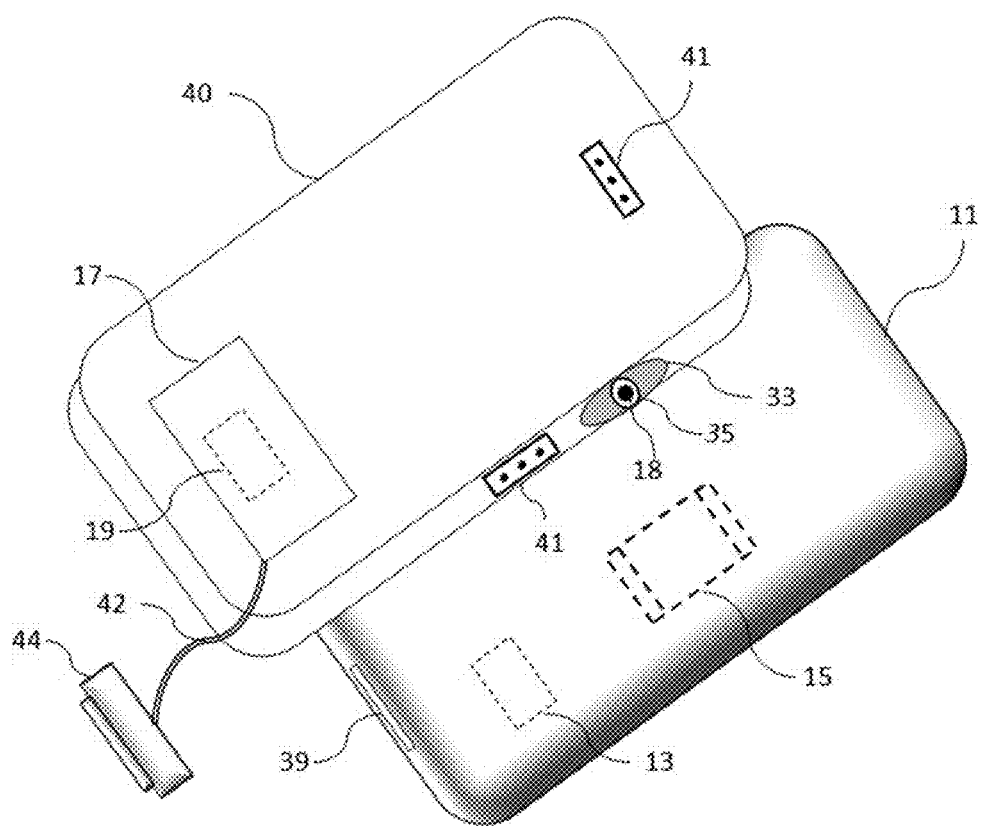
FIG. 4 illustrates an embodiment of an emotion monitoring device based on a cover incorporating biosensors that attaches and connects to a mobile phone.

Referring to FIG. 4, an embodiment of EMD 10 is shown in which the biosensors are incorporated in a cover 40 that is designed to slip over or snap on a mobile phone 11. The cover is equipped with similar biosensors 18, or a dispersion of biosensors 41, finger depressions 33, and contact sensors 35, as described in the previous embodiment. The biosensors are connected to SPU 17 which amplifies and processes the physiological signals to remove artifact as described above. The signals are coupled by means of cable 42 to connector 44 that plugs into the generic input/output port 39 of the mobile phone 11. SPU 17 and connector 44 may be combined in one unit. Alternatively, SPU 17 may connect with mobile phone 11 by means of a short-range wireless transmitter 19 (e.g. Bluetooth®). An application program 15 running on the mobile phone 11 derives emotion data. Alternatively, the emotion-deriving algorithms may be implemented in firmware in SPU 17 or connector 44. The emotion data can be displayed, transmitted to the Internet, stored on a server, and shared with other users, as described in the previous embodiments.

It will be apparent to one of ordinary skill in the art that, in place of mobile phone 11, a cover can be designed for other types of handheld devices, such as a tablet, game controller, TV remote controller, motion detector, or computer mouse. On some devices, the cover may be in the form of a sleeve that fits over or on or in part of the device (e.g., on the handles of a game controller) or is in the form of a pad attached by means of adhesive.

Figure 5:
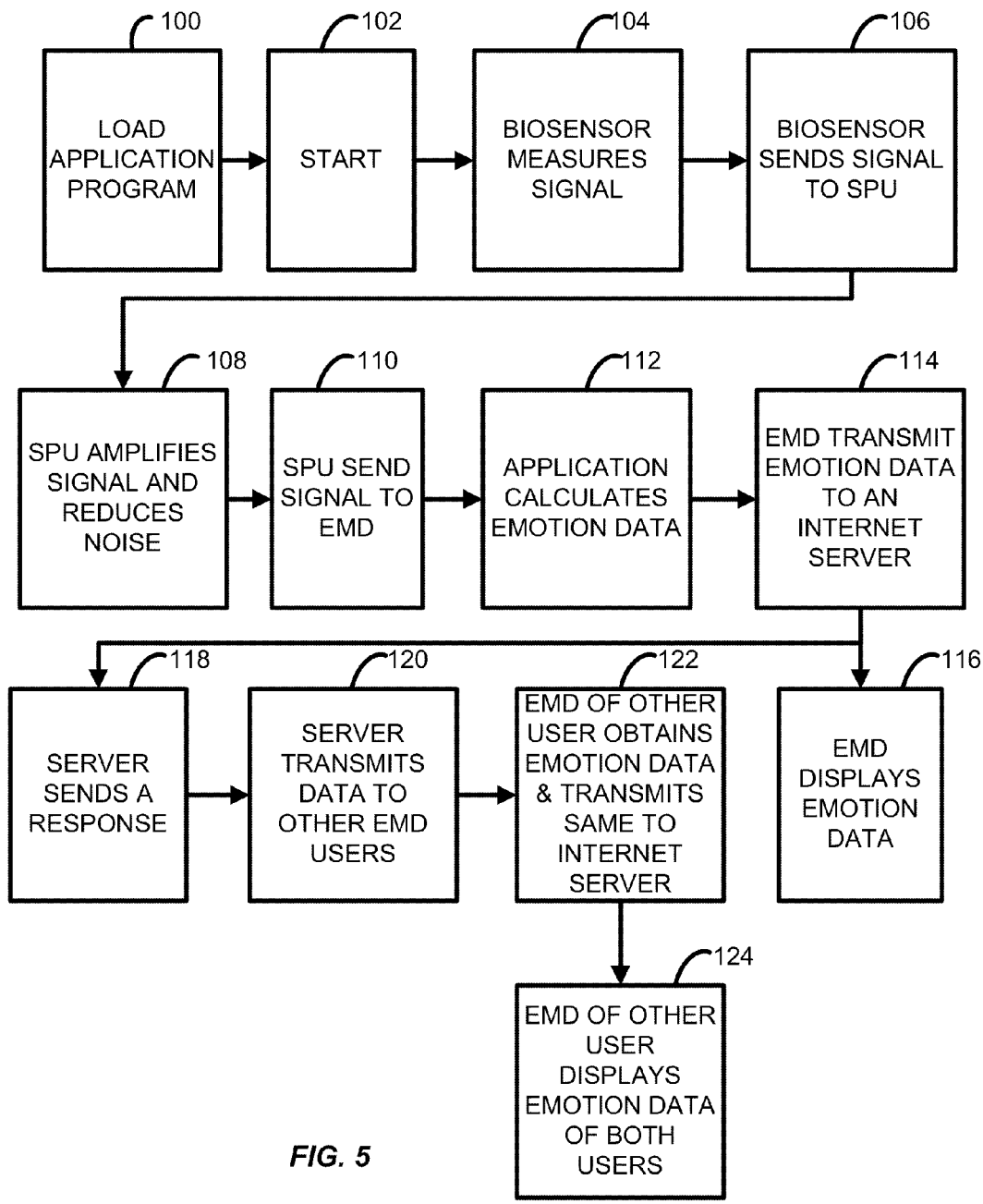
FIG. 5 illustrates a diagram of data flow in an emotion monitoring network according to a general embodiment of the invention.

Referring to FIG. 5, an emotion monitoring network is illustrated. A user starts an application program (which in some implementations may constitute a very thin client, while in others may be very substantial) in an EMD (step 102), the application program having been previously loaded into the EMD (step 100). A biosensor measures a physiological signal (step 104). The biosensor sends the signal to a SPU (step 106) which amplifies the signal and reduces artifact and noise in the signal (step 108). The SPU transmits the processed signal via a wired or wireless connection to the EMD (step 110). The EMD further processes the signal and calculates a variety of emotion related data, such as emotional arousal and valence measures (step 112). The EMD displays the emotion data to the user (step 116) and transmits the emotion data to an internet server via a telecommunications network (step 114). An application program resident on the internet server processes the emotion data and sends a response to the user (step 118). It should be noted that the application program may reside on one or more servers or cloud infrastructure connected to the internet and the term "response" here is used generally. The internet server then transmits the emotion data to one or more remote users equipped with an EMD (step 120) where the emotion data is displayed (step 124). The remote user's EMD similarly calculates their emotion data from physiological signals and transmits it to an internet server to be shared with other users (step 122). The sharing may be accomplished in a number of ways, and for a number of purposes. In some cases, aggregate emotional data may be combined and analyzed statistically according to the requirements of the user. In other cases, individual emotional data may be employed to notify another user or a group of users of an individual or subject user's emotional state. In still other cases, individual emotional data may be employed to control an avatar in or other aspects of a multiplayer game. In general, a signal corresponding to emotional data may be employed as the basis for calculation, where the calculation is in a videogame, social community, control system, or the like.

It will be understood that the above description of the apparatus and method has been with respect to particular embodiments of the invention. While this description is fully capable of attaining the objects of the invention, it is understood that the same is merely representative of the broad scope of the invention envisioned, and that numerous variations of the above embodiments may be known or may become known or are obvious or may become obvious to one of ordinary skill in the art, and these variations are fully within the broad scope of the invention. For example, while certain wireless technologies have been described herein, other such wireless technologies may also be employed. In another variation that may be employed in some implementations of the invention, the measured emotion data may be cleaned of any metadata that may identify the source. Such cleaning may occur at the level of the mobile device or at the level of the secure server receiving the measured data. In addition, it should be noted that while implementations of the invention have been described with respect to sharing emotion data over the internet, e.g. for social networking purposes or for gaming purposes, the invention also encompasses systems in which no such sharing is performed. For example, a user may simply wish to receive a quantitative display of measurements corresponding to their own or another's emotional response over a time period or to a specific stimulus. Accordingly, the scope of the invention is to be limited only by the claims appended hereto, and equivalents thereof. In these claims, a reference to an element in the singular is not intended to mean "one and only one" unless explicitly stated. Rather, the same is intended to mean "one or more". All structural and functional equivalents to the elements of the above-described preferred embodiment that are known or later come to be known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present invention is intended to be dedicated to the public regardless of whether the element, component, or method step is explicitly recited in the claims.

The invention claimed is:

1. A method for monitoring emotion data in a network using a mobile phone, comprising:
  a. downloading an application to a mobile phone from an internet server, the application configured to receive a physiological signal from a biosensor and process the signal to reduce the presence of artifacts;
  b. running the application in the mobile phone, and receiving a physiological signal;
  c. computing emotion data from the received physiological signals using the downloaded application, the computed emotion data including a component of emotional arousal or a component of emotional valence or both;
  d. displaying the computed emotion data using the downloaded application;
  e. transmitting the emotion data to an internet server using a wireless network;
  f. receiving a response from the internet server; and
  g. displaying the response on the mobile phone on a user interface associated with the downloaded application.

2. A non-transitory computer readable medium, comprising instructions for causing a computer device to perform the method of claim 1.

3. A method for monitoring emotion data in a network from a mobile device, comprising:
  a. upon request, downloading an application to a mobile device, the application including instructions to configure the mobile device to receive a signal from one or more biosensors;
  b. receiving emotion data from the downloaded application from one or more mobile devices, the emotion data including a component of emotional arousal or a component of emotional valence or both; and
  c. transmitting data corresponding to the received emotion data to one or more other mobile devices running the downloaded application, including data corresponding to the component of emotional arousal or the component of emotional valence or both.

4. A non-transitory computer readable medium, comprising instructions for causing a computer device to perform the method of claim 3.

5. An emotion monitoring device in the form of a mobile phone connected in a wired or wireless fashion to a biosensor, the device including a non-transitory computer readable medium comprising instructions for causing the device to perform the following steps:
  a. receive physiological signals from a biosensor, the biosensor structured and configured to facilitate finger contact, and process the signals to reduce artifacts;
  b. instantiate an application in the mobile phone;
  c. compute emotion data from the received physiological signals, the emotion data including a component of emotional arousal or a component of emotional valence or both;
  d. display the emotion data;
  e. transmit the emotion data to an internet server using a wireless network;
  f. receive a response from the internet server; and
  g. display the response on the mobile phone.

6. The device of claim 5, wherein the received response includes emotion data from other users.

7. The device of claim 5, wherein the instantiated application performs the steps of receiving physiological signals from a biosensor, and processing the signals to reduce artifacts.

8. An emotion monitoring device in the form of a mobile phone with biosensors integrated in a casing, the device including a non-transitory computer readable medium comprising instructions for causing the device to perform the following steps:
  a. receive physiological signals from a biosensor, the biosensor integrated in a casing of a mobile phone, the biosensor structured and configured to facilitate finger contact, and process the signals to reduce artifact;

b. instantiate an application in the mobile phone;

c. compute emotion data from the received physiological signals, the emotion data including a component of emotional arousal or a component of emotional valence or both;

d. display the emotion data;

e. transmit the emotion data to an internet server using a wireless network;

f. receive a response from the internet server; and g. display the response on the mobile phone.

9. The device of claim 8, wherein the received response includes emotion data from other users.

10. The device of claim 8, wherein the instantiated application performs the steps of receiving physiological signals from a biosensor, and processing the signals to reduce artifact.

11. An emotion monitoring device in the form of a cover, sleeve, or attachment and configured to fit a mobile phone, the cover, sleeve, or attachment incorporating a biosensor and configured to be in signal communication with the mobile phone, the device or the mobile phone or both including a non-transitory computer readable medium comprising instructions for causing the combination device and mobile phone to perform the following steps:

a. receive physiological signals from a biosensor via a direct wired or radio frequency connection, the biosensor incorporated within a cover, sleeve, or attachment configured to fit a mobile phone, the biosensor structured and configured to facilitate finger contact, and process the signals to reduce artifact;

b. instantiate an application in the mobile phone;

c. compute emotion data from the received physiological signals, the emotion data including a component of emotional arousal or a component of emotional valence or both;

d. display the emotion data;

e. transmit the emotion data to an internet server using a wireless network;

f. receive a response from the internet server; and g. display the response on the mobile phone.

12. The device of claim 11, wherein the received response includes emotion data from other users.

13. The device of claim 11, wherein the instantiated application performs the steps of receiving physiological signals from a biosensor, and processing the signals to reduce artifact.

14. A non-transitory computer readable medium, comprising instructions for causing a processor in a mobile phone to perform a method of processing data relating to emotion, comprising:

a. receiving data relating to emotion, the emotion data including a component of emotional arousal or a component of emotional valence or both;

b. displaying the emotion data;

c. transmitting the emotion data to an internet server using a wireless network;

d. receiving a response from internet server; and e. displaying the response on the mobile phone, f. wherein the displaying the received response and at least one of the receiving data, displaying data, or transmitting data are performed by an application running on the mobile phone, the application downloaded from an internet server.

15. A method for monitoring emotion data in a network from a computing device, comprising:

a. upon request, downloading an application to a computing device, the application including instructions to configure the computing device to receive a signal from a sensor;

b. receiving emotion data from the downloaded application running on one or more computing devices, the emotion data including a component of emotional arousal or a component of emotional valence or both;

c. and d. transmitting data corresponding to the received emotion data to one or more other computing devices running the downloaded application, including data corresponding to the component of emotional arousal or the component of emotional valence or both;

e. wherein the computing device is a personal computer, a game console, a wearable mobile device, or a hardware appliance programmed for this use.

16. An emotion monitoring device in the form of a computing device connected in a wired or wireless fashion to a sensor, the device including a non-transitory computer readable medium comprising instructions for causing the device to perform the following steps:

a. receive signals from a sensor;

b. instantiate an application in the computing device;

c. compute emotion data from the received signals, the emotion data including a component of emotional arousal or a component of emotional valence or both;

d. display the emotion data;

e. transmit the emotion data to an internet server using a wireless network;

f. receive a response from the internet server; and g. display the response, h. wherein the computing device is a personal computer, a game console, a wearable device, or a hardware appliance programmed for this use.

* * * * *